(12) United States Patent
Raymond et al.

(10) Patent No.: US 6,626,928 B1
(45) Date of Patent: Sep. 30, 2003

(54) OCCLUSION DEVICE FOR TREATING ANEURYSM AND USE THEREFOR

(75) Inventors: Jean Raymond, Montréal (CA); Guy Leclerc, Rosemère (CA)

(73) Assignees: Angiogene, Inc., Montreal (CA); Corporation du Centre de Recherche L'Universite de Montreal, Montreal (CA)

(*) Notice: Subject to any disclaimer, the term of this patent is extended or adjusted under 35 U.S.C. 154(b) by 0 days.

(21) Appl. No.: 09/510,797

(22) Filed: Feb. 23, 2000

(51) Int. Cl.$^7$ ............................................. A61M 29/00
(52) U.S. Cl. ........................ 606/200; 623/1.1; 623/1.34; 600/3
(58) Field of Search ................... 606/200, 151; 600/1, 3, 4; 623/1.1, 1.34; 128/898

(56) References Cited

U.S. PATENT DOCUMENTS

| | | | |
|---|---|---|---|
| 5,059,166 A | 10/1991 | Fischell et al. | ............... 600/3 |
| 5,122,136 A | 6/1992 | Guglielmi et al. | ............ 606/32 |
| 5,722,984 A | 3/1998 | Fischell et al. | ............. 606/199 |
| 6,015,541 A * | 1/2000 | Greff et al. | ..................... 600/3 |
| 6,231,590 B1 * | 5/2001 | Slaikeu et al. | .............. 606/200 |
| 6,287,249 B1 * | 9/2001 | Tam et al. | ...................... 600/3 |

FOREIGN PATENT DOCUMENTS

| | | | |
|---|---|---|---|
| WO | WO 93/08767 | 5/1993 | ............. A61F/2/06 |
| WO | WO 98/12990 | 4/1998 | ............. A61F/2/06 |
| WO | WO 99/61107 | 12/1999 | |

OTHER PUBLICATIONS

Jean Raymond et al., *Neurosurgery*, 41:6, 1997.

* cited by examiner

*Primary Examiner*—Julian W. Woo
(74) *Attorney, Agent, or Firm*—Nixon Peabody LLP

(57) ABSTRACT

The present invention relates to an occlusion device for treating an aneurysm, its use and a method for treating an aneurysm. The occlusion device comprises a detachable filling element and at least one radioactive source. The detachable filling element and the radioactive source are adapted to be inserted into a vessel at least in close proximity of a neck of an aneurysm. The radioactive source stimulates neointima formation for obstructing the neck of the aneurysm or filling up the aneurysm.

8 Claims, 2 Drawing Sheets

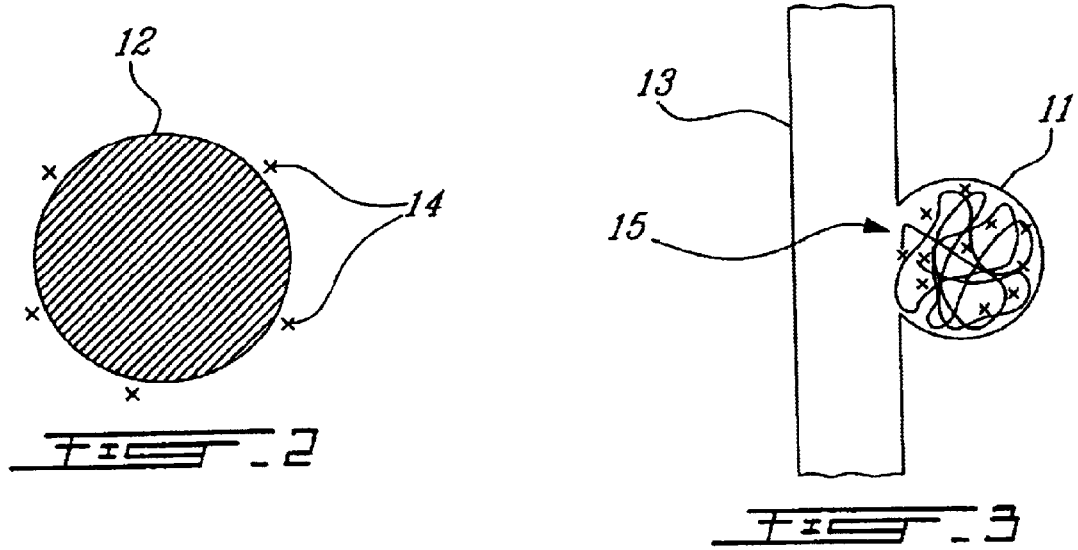
FIG. 2
FIG. 3
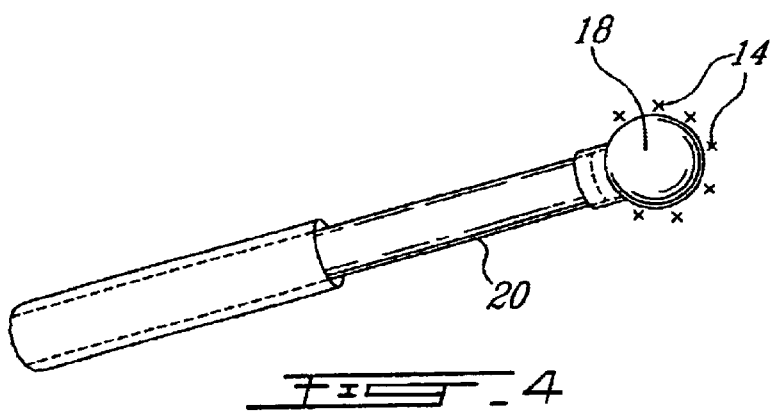
FIG. 4
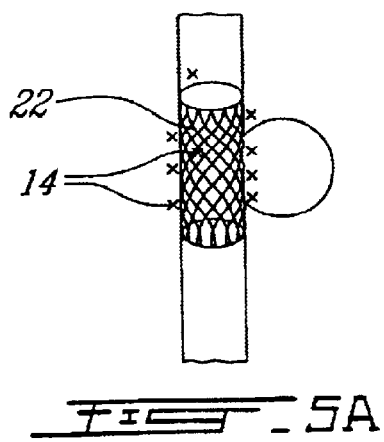
FIG. 5A
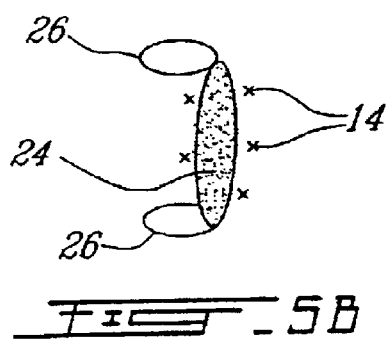
FIG. 5B

OCCLUSION DEVICE FOR TREATING ANEURYSM AND USE THEREFOR

BACKGROUND OF THE INVENTION (a) Field of the Invention

The invention relates to an artificial occlusion device designed for the endovascular treatment of aneurysms, such as intracranial, or for closing any body lumen, such as vascular lumen or other. The invention also relates to the use of the occlusion device and a method for treating an aneurysm.

(b) Description of Prior Art

Direct surgical clipping has been used for the treatment of most intracranial aneurysms. However, surgical difficulties and related morbidity with certain aneurysms have stimulated the development of endovascular procedures. Despite the favorable results of endovascular platinum coil treatment in acutely ruptured aneurysms, neck remnants and recurrences are frequent and may compromise the long term success of this treatment modality (Jean Raymond et al., *Neurosurgery*, 41:6, 1997). This mechanical failure of the device of the prior art is not surprising and coils alone without efficient healing mechanisms may not be strong enough to counteract the continuous repetitive force of the abnormal flow which often remains following incomplete endovascular treatment.

The mechanism of surgical clipping directly apposes the vessel wall, leading to rapid "primary healing". By opposition, following endovascular treatment, the wound margins are separated by coils and healing depends on fibrous replacement of clot between coils and growth of a neointima at the coil—parent vessel interface. There is a general pattern of wound healing in the vessel wall, which occurs following a wide variety of traumatic or pathological conditions. These mechanisms are also involved in repairing experimental aneurysms. In vivo studies suggest that healing of experimental aneurysms involves coagulation, inflammation, cellular migration, proliferation, matrix secretion with the formation of a neointima at the neck of treated aneurysms. The proposed invention is designed to increase neointima formation at the neck of treated lesions in order to improve long-term results of endovascular treatment.

Intracranial aneurysms can be treated by four different principles:

1) Surgical clipping permits closure of the aneurysmal neck from the outside, with close apposition of the edges of the "wound" and satisfactory healing, but necessitates craniotomy and dissection at the base of the brain.

2) Parent vessel occlusion consisting of occlusion of the vessel along with the aneurysm or with the intent to decrease blood flow to the aneurysm, is possible only in certain anatomical sites, and in the presence of an adequate collateral circulation.

3) Parent vessel stenting is a new possibility but is currently technically feasible only in proximal vessels or in extracranial aneurysms such as the aorta (WO 98/12990 and WO 93/08767).

4) Selective endosaccular occlusion of the aneurysm is currently the most frequently used method of endovascular treatment. This method can be performed with three (3) different types of material:

a) Liquid or fluid agents which polymerize inside the aneurysm or immediately before exiting the catheter; this strategy has never been routinely used because of the fear of cerebral embolization;

b) Detachable balloons have been introduced by Serbinenko, Romodanov and Scheghlov and have more frequently been used between 1978 to 1990. The expertise necessary for using these devices was difficult to master; these devices led to a high incidence of inadvertent aneurysm rupture and were also plagued with a high incidence of recurrences; and c) Microcoils; these metallic devices became popular with the Guglielmi Detachable Coil system, which permitted to reposition the coil and detach it only when it was felt to be in a satisfactory position. The availability of this system has greatly increased the use of the endovascular route in the treatment of intracranial aneurysms. This device is much safer to use than detachable balloons, free coils, or polymeric embolic agents. The main advantage of soft coils compared to detachable balloons is the fact that they will conform to the shape of the aneurysm. However, even in aneurysms which can be sufficiently occluded in order to prevent rebleeding of the aneurysm during the acute phase, recurrences after a few months are& frequent and this fear of recurrences is currently the major drawback of the technique and the most important argument against a more widespread clinical application.

It would be highly desirable to be provided with a device for treating aneurysms, which could stimulate neointima formation at the neck of treated aneurysms for improving long-term results of endovascular treatment.

It would also be highly desirable to be provided with a method for treating aneurysms, which could increase neointima formation at the neck of treated aneurysms for improving long-term results of endovascular treatment.

SUMMARY OF THE INVENTION

One aim of the present invention is to provide a device for treating aneurysms, which could stimulate neointima formation at the neck of treated aneurysms for improving long-term results of endovascular treatment.

Another aim of the present invention is to provide a method for treating aneurysms, which could increase neointima formation at the neck of treated aneurysms for improving long-term results of endovascular treatment.

In accordance with the present invention there is provided a device for treating aneurysms, which could stimulate neointima formation at the neck of treated aneurysms for improving long-term results of endovascular treatment.

In accordance with the present invention there is provided a method for treating aneurysms, which could increase neointima formation at the neck of treated aneurysms by emission of radiation.

Still in accordance with the present invention there is provided an occlusion device for treating an aneurysm, comprising a detachable filling element and at least one radioactive source, said detachable filling element and said radioactive source being adapted to be inserted into a vessel at least in close proximity of a neck of an aneurysm, said radioactive source stimulating neointima formation for obstructing the neck of the aneurysm or filling up the aneurysm.

The detachable filling element may be a coil, preferably a platinum coil.

The radioisotope source is preferably a β-emitting source. The radioisotope source may be made of a polymer and a radioisotope. The β-emitting source is preferably at least one β-emitting source from Antimony-124, Cesium-134, Cesium-137, Calcium-45, Calcium-47, Cerium 141, Chlorine-36, Cobalt-60, Europium-152, Gold-198, Hafnium-181, Iodine-131, Iridium-192, Iron-59, Lutetium-177, Mercury-203, Neodymium-147, Nickel-63, Phosphorus-32, Phosphorus-33, Rhenium-186, Rubidium-86, Ruthenium-106, Samarium-153, Scandium-46, Silver-110m, Strontium-89, Strontium-90, Sulfur-35, Technetium-99, Terbium-160, Thulium-170, and Yttrium-90.

In accordance with another aspect of the invention, the occlusion device may further comprise a second filling element selected from the group consisting of a coil, a polymer, a bioactive peptide, an aqueous solution, and a gel. The aqueous solution is preferably a polymerizable solution capable of polymerization once in the aneurysm.

Further in accordance with the present invention, there is provided the use of an occlusion device as defined above for the treatment of an aneurysm.

Also in accordance with the present invention, there is provided a kit for the treatment of an aneurysm. The kit comprises:
 a detachable filling element adapted to be inserted into a vessel at least in close proximity with a neck of an aneurysm; and
 a radioactive source adapted to be inserted with the detachable filling element;
 wherein the radioactive source stimulates neointima formation causing obstruction of the neck of the aneurysm or filling up the aneurysm.

Further in accordance with the present invention, there is provided a method for treating an aneurysm comprising inserting a detachable filling element and a radioactive source into a vessel at least in close proximity of a neck of an aneurysm, the radioactive source stimulating neointima formation causing obstruction of the neck of the aneurysm or filling up the aneurysm.

BRIEF DESCRIPTION OF THE DRAWINGS

Having thus generally described the nature of the invention, reference will now be made to the accompanying drawings, showing by way of illustration a preferred embodiment thereof, and wherein:

FIG. 2 is an enlarged cross-sectional view taken along lines 2—2 of FIG. 1;

FIG. 3 is partial schematic cross-sectional view of an artery having an aneurysm filled with the radioactive coil of FIG. 1;

FIG. 4 is a schematic view of another embodiment of the invention; and

FIGS. 5A and 5B illustrate a schematic view of further embodiments of the invention.

DETAILED DESCRIPTION OF THE INVENTION

Figure 1:
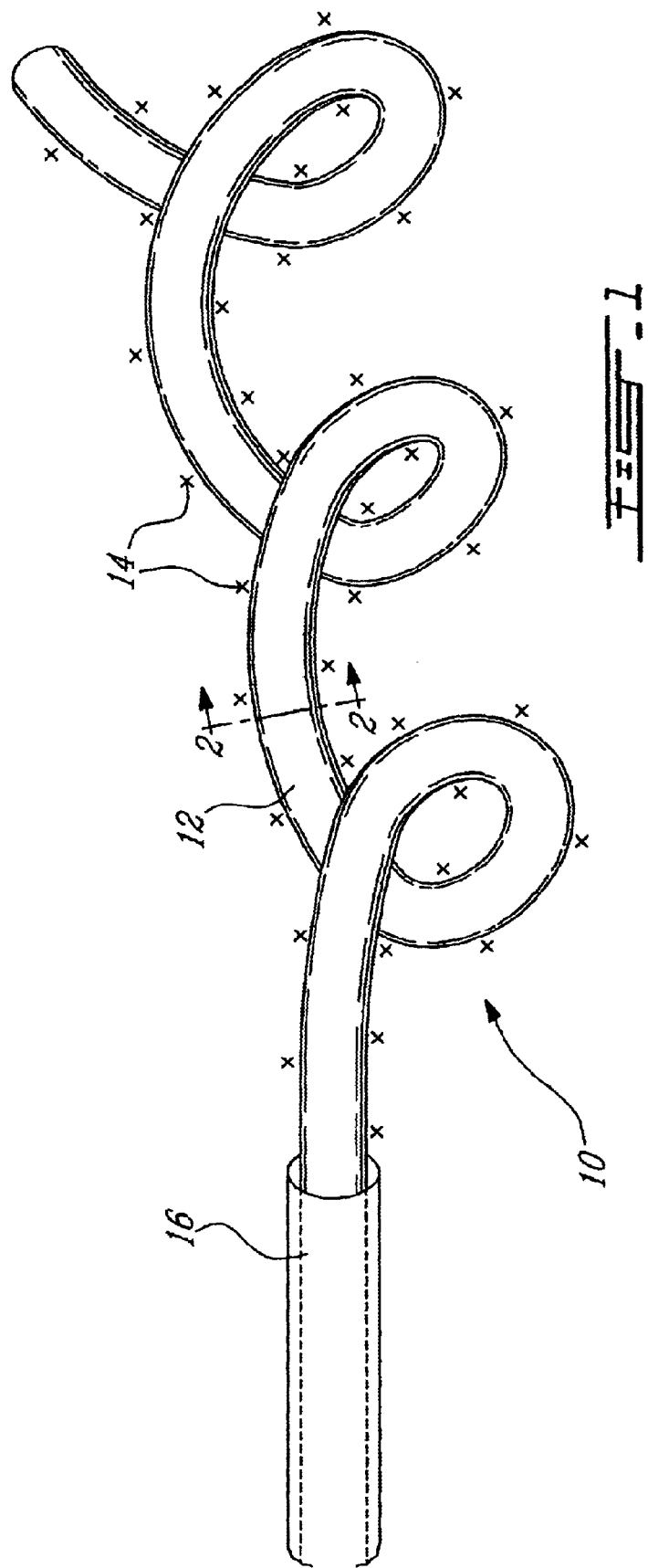
FIG. 1 is a partial schematic representation of a microcatheter provided with a radioactive coil in accordance with one embodiment of the invention.

In accordance with one embodiment of the present invention there is provided a device for treating aneurysm, which would increase neointima formation in aneurysms treated endovascularly by adding a radioactive source to the embolic agent. Since mechanisms involved in healing aneurysms are similar to neointimal hyperplasia after balloon injury, the inventors found that an embolic material emitting β-particles promotes healing in situations where mechanisms are deficient, such as after endovascular treatment of intracranial aneurysms in clinical practice. Although β-particle emitting stents have been designed to inhibit neointima formation, 1 $\mu$Ci and lower dose stents are shown to cause the reverse effect i.e. they were associated with a more severe neointimal response than control stents. Neointima formation may be promoted with low dose radiation by fibrin-thrombus deposition, overexpression of tissue factor, inflammation and growth factor secretion by inflammatory cells, by stimulation of extracellular matrix by neointimal cells or by any other unknown mechanisms. Thus a radioactive source that is delivered at low dose increases neointima formation at the neck of the aneurysms. This stimulation would then decrease the incidence of recurrence.

As seen in FIGS. 1 to 3, in accordance with one embodiment of the present invention, there is provided an artificial occlusion device 10 designed for endovascular treatment o: an aneurysm 11, and preferably of an intracranial aneurysm. However, the artificial occlusion device 10 is not restricted to this use as it could also be used to close any body lumen, such as vascular lumen or others. The artificial occlusion device 10 comprises a detachable filling coil 12, onto which a β-emitting radioactive source 14, such as $^{32}$P, is coated.

In this embodiment, the embolic agent is a detachable coil, preferably a platinum coil, and the radioactive source is $^{32}$P, a β-emitting isotope of phosphorus. In one embodiment of the invention, $^{32}$P ions are directly coated onto the metallic coil, using ion implantation. A beam of $^{32}$P ions is accelerated to hundreds of Kev and directed along a beam line to the coil surface, Direct implantation of $^{32}$P to reach a total activity in the range of 1 $\mu$Ci is envisioned, although the dose may vary. Penetration of $^{32}$P ions is only a few tenths of a micron, so that the trace amounts are not expected to alter significantly the properties of the coil. Other γ or β emitters such as rhenium, strontium, or any other radioactive source can be used for the same purpose. The radioactive source can be part of a large molecule, or can be added to a polymer. or a chemical substance used to coat the surface or to fill the center of coils.

The radioactive source can be delivered through a polymer or any filling.substance that could be used as an embolic agent, either alone or in combination with a coil.

In use the filling coil 12 and the β-emitting radioactive source 14 are delivered with a microcatheter 16. For filling the aneurysm 11 with the artificial occlusion device 10, the same procedure is done as is presently being done for filling any aneurysm. The difference being that currently, aneurysms are being filled with a filling coil alone, whereas in accordance with the present invention, aneurysm treated with the present invention would be filled with a filling coil coated or ion implanted with a β-emitting radioactive source, realizing in fact a local intra-aneurysmal radiotherapy.

Briefly, the microcatheter 16 is brought to the aneurysm 11 to be treated from within a blood vessel 13. At the site of the aneurysm 11, the filling coil 12 carrying (such as coated or ion implanted with) a β-emitting radioactive source 14 is pushed in the aneurysm 11. Sufficient filling coil 12 is inserted in the aneurysm 11 for filling and packing it. The β-emitting radioactive source 14 on the filling coil 12 stimulates neointima formation, which will cause the closing of the neck 15 of the aneurysm 11 therefore repairing the blood vessel.

In another embodiment of the present invention, the β-emitting radioactive source 14 is coated onto the surface of a detachable balloon 18, as illustrated in FIG. 4 for treating aneurysms. The detachable balloon is mounted on a delivery wire 20 or catheter slidably fitted into the microcatheter 16. Accordingly, when the pushing wire 20 is retracted into the microcatheter 16, the balloon 18 coated with the β-emitting radioactive source 14 is detached from the pushing wire 20, and left into the aneurysm.

In a further embodiment of the present invention as illustrated in FIG. 5A, there is provided a stent 22 coated with the β-emitting radioactive source 14. The stent is inserted within the blood vessel as is being done in the art. The radioactive source on the stent stimulates neointima formation. After a period of time, the stent will be embedded in a new neointima formation, which will therefore obstruct the neck of the aneurysm, causing same to close.

A variant of this latter embodiment is illustrated in FIG. 5B. In FIG. 5B, a support 24 coated with a radioactive source 14 is mounted at each ends thereof on an self-expandable loop 26, each adapted to fractionally engage with the inner surface of a blood vessel for maintaining the support 24 in place with the blood vessel.

Accordingly, the variant is installed similarly as a stent is installed, positioning however the support 24 coated with a radioactive source 14 against the neck of an aneurysm for obstructing same. As mentioned previously, after a given time, the support 24 will be covered by a neointima formation, which will cause closing of the neck of the aneurysm.

While the invention has been described with particular reference to the illustrated embodiment, it will be understood that numerous modifications thereto will appear to those skilled in the art. Accordingly, the above description and accompanying drawings should be taken as illustrative of the invention and not in a limiting sense,

What is claimed is:

1. An occlusion device for treating an aneurysm, comprising a detachable first filling element, at least one radioactive source, and a second filling element, said detachable first filling element, said radioactive source and said second filling element being adapted to be inserted into a vessel at least in close proximity of a neck of an aneurysm, said first filling element being a coil or a stent, said radioactive source comprising a polymer and a radioisotope for stimulating neointima formation for obstructing the neck of the aneurysm or filling up the aneurysm, and said second filling element being selected from the group consisting of a polymer, a bioactive peptide, an aqueous solution, and a gel.

2. The occlusion device of claim 1, wherein the detachable first filling element is a coil.

3. The occlusion device of claim 2, wherein said coil is a platinum coil.

4. The occlusion device of claim 1, wherein the radioactive source is a β-emitting source.

5. The occlusion device of claim 4, wherein the β-emitting source is at least one β-emitting source selected from the group consisting of Antimony-124, Cesium-134, Cesium-137, Calcium-45, Calcium-47, Cerium 141, Chlorine-36, Cobalt-60, Europium-152, Gold-198, Hafnium-181, Iodine-131, Iridium-192, Iron-59, Lutetium-177, Mercury-203, Neodymium-147, Nickel-63, Phosphorus-32, Phosphorus-33, Rhenium-186, Rubidium-86, Ruthenium-106, Samarium-153, Scandium-46, Silver-110m, Strontium-89, Strontium-90, Sulfur-35, Technetium-99, Terbium-160, Thulium-170, and Yttrium-90.

6. The occlusion device of claim 1, wherein the aqueous solution is a polymerizable solution capable of polymerization once in the aneurysm.

7. A method for treating an aneurysm comprising inserting a detachable first filling element, with a radioactive source and a second filling element into a vessel at least in close proximity of a neck of an aneurysm, said radioactive source comprising a polymer and a radioisotope for stimulating neointima formation causing obstruction of the neck of the aneurysm or filling up the aneurysm.

8. A kit for the treatment of an aneurysm, said kit comprising:

a) a detachable first filling element adapted to be inserted into a vessel at least in close proximity with a neck of an aneurysm, said first detachable filling element being a coil or a stent;

b) a radioactive source adapted to be inserted together with the detachable filling element and comprising a polymer and a radioisotope; and c) a second filling element also adapted to be inserted into the vessel at least in close proximity with the neck of the aneurysn;

wherein said radioactive source is adapted to neointima formation causing obstruction of the neck of the aneurysm or filling up the aneurysm.

* * * * *